(12) United States Patent
Chang et al.

(10) Patent No.: US 9,474,892 B2
(45) Date of Patent: Oct. 25, 2016

(54) METHOD AND SYSTEM FOR DECREASING TRANSTHORACIC IMPEDANCE FOR CARDIOVERSION AND DEFIBRILLATION

(71) Applicant: NEXUS CONTROL SYSTEMS, LLC, Port Washington, NY (US)

(72) Inventors: Aaron Chang, Grand Prairie, TX (US); Melinda Chen, Lutherville, MD (US); Piyush Poddar, Cranbury, NJ (US); Rohil Malpani, Kolkata (IN); Peter Malamas, Jamison, PA (US); Sandya Subramanian, Grand Rapids, MI (US); Joon Eoh, College Station, TX (US); Kevin George, Santa Fe Springs, CA (US); Todd J. Cohen, Port Washington, NY (US)

(73) Assignee: Nexus Control Systems, LLC, Port Washington, NY (US)

( * ) Notice: Subject to any disclaimer, the term of this patent is extended or adjusted under 35 U.S.C. 154(b) by 0 days.

(21) Appl. No.: 14/536,293

(22) Filed: Nov. 7, 2014

(65) Prior Publication Data
US 2015/0221205 A1    Aug. 6, 2015

Related U.S. Application Data

(60) Provisional application No. 61/902,268, filed on Nov. 10, 2013.

(51) Int. Cl.
*G08B 21/00*    (2006.01)
*A61N 1/04*    (2006.01)
*A61N 1/39*    (2006.01)
*A61H 1/00*    (2006.01)

(52) U.S. Cl.
CPC ............. *A61N 1/046* (2013.01); *A61N 1/3931* (2013.01); *A61H 1/00* (2013.01)

(58) Field of Classification Search
CPC .................................. A61N 1/00; A61H 1/00
See application file for complete search history.

(56) References Cited

U.S. PATENT DOCUMENTS

2014/0163663 A1* 6/2014 Poddar ................. A61N 1/0476
                                                    607/142

\* cited by examiner

*Primary Examiner* — Shirley Lu
(74) *Attorney, Agent, or Firm* — William Dippert; Laurence Greenberg; Werner Stemer

(57) ABSTRACT

A method and system for improving the effectiveness of cardioversion and defibrillation through the ability to reduce transthoracic impedance. A method and system of decreasing transthoracic impedance that allows standardized pressure to be applied directly over desired defibrillator patches. This system reduces transthoracic impedance by increasing effective pressure on desired patches through use of a manual depressor device which incorporates a deformable patient body interface and mechanical and or electronic mechanisms to provide qualitative and or quantitative feedback on the force being applied to said patches. By depressing the device over desired external adhesive electrode patches until an audio and or visual signal indicates sufficient applied pressure, increased patch to skin contact is achieved to decrease the effective transthoracic impedance of a patient upon delivery of a defibrillation shock.

16 Claims, 2 Drawing Sheets

METHOD AND SYSTEM FOR DECREASING TRANSTHORACIC IMPEDANCE FOR CARDIOVERSION AND DEFIBRILLATION

FIELD OF THE INVENTION

This invention relates to devices used in procedures of cardioversions and defibrillations and in particular to methods of reducing transthoracic impedance during said procedures.

BACKGROUND OF THE INVENTION

Cardiac arrhythmias currently affect over 14 million and claim the lives of an estimated 450,000 people each year in the US. Two common treatments for arrhythmia patients are cardioversion and defibrillation. In these treatments, clinicians deliver high-energy electrical shocks to the heart to convert it to normal sinus rhythm. However, there is no guarantee that any given shock will work; if a given shock does not work, clinicians must make decisions, often in a matter of seconds, on what to do to increase the chance of success on the next shock. If the first shock fails, the current standard of care dictates that the only easily accessible option clinicians have is to increase the energy of the shock. However, this practice can cause unnecessarily pain for the patient without ensuring increased success. According to literature, less harmful but possibly equally effective alternatives, such as switching shock vectors or reducing transthoracic impedance, exist. Unfortunately, these alternatives are out of reach because there is no safe, standardized way to implement them quickly.

In particular, observed methods of decreasing transthoracic impedance in cardioversion settings have been observed to be unstandardized and crude. Physicians have been observed to use various mechanisms to apply pressure over desired external electrode patches such as using their fist, pushing down on patches with folded towels, or even using other non-related clinical implements such as urinal bottles. The effect of applying pressure over external adhesive electrode patches is to increase the quality of patch to skin contact, therein increasing adhesion and reducing the effective transthoracic impedance while delivering a defibrillator shock. It is clear that physicians acknowledge the utility of decreasing the transthoracic impedance before defibrillation, but the quality of the transthoracic impedance reduction is currently unknown as current standards do not provide quantitative or qualitative feedback on the amount of pressure exerted. Furthermore, current common practices contradict common resuscitation guidelines to clear the patient area and step away from the patient before delivering a defibrillator shock. In particular, the current unstandardized methods of impedance reduction have been observed to necessitate physicians to stay in close proximity to the patient throughout the duration of the shock, therein increasing the risk of accidental shock of the physician.

The field of this invention lies in the area of reducing transthoracic impedance through the application of standardized pressure, and the prior art contains a few objects of note. One method of reducing transthoracic impedance falls under the category of applying external pressure to the thoracic cavity. WO1992000716 A1 refers to an external cardiac massage device which applies rhythmic pressure to the sternum. Similarly, CA2066297 C refers to devices and methods for external chest compression which maintain a minimum residual pressure on the patient throughout the compression cycle. CA2117275 C and U.S. Pat. No. 5,891,062 refer to methods of active compression and decompression of the chest for CPR while using plunger-inspired patient body interfaces, while also utilizing a force gauge to monitor quality of CPR compressions. Furthermore, US20130060173 A1 refers to a method of providing CPR compressions to a patient which utilizes accelerometer data to determine the depth of compression.

Although the prior art shows mechanisms of applying rhythmic pressure to the sternum during resuscitation, there is currently no standardized method for the purposes of reducing transthoracic impedance when using external defibrillation adhesive electrode patches, and thus the intellectual property landscape is clear.

OBJECTS OF THE INVENTION

It is an object of the invention to provide a method and system of decreasing transthoracic impedance for cardioversion and defibrillation comprising:

a device incorporating a deformable patient body interface joined by an increased diameter junction to a rigid lower plate; a compression zone having a top and bottom end wherein the bottom end is attached to the lower plate and the top end is attached to the top plate, therein enclosing semi-elastic mechanisms or materials and a force feedback system; a top plate with an attached handle and embedded user interface that provides feedback to the user, characterized in that when the deformable patient body interface is compressed against the patient's body with a standardized calibrated threshold force, an indicator cue will notify the user.

It is an object of the invention to provide a method and system of decreasing transthoracic impedance for cardioversion and defibrillation, wherein the deformable patient body interface is comprised of an elastic and or moldable material which comforms to non-uniform surfaces, such as the body of a patient, upon compression and can return to its original shape upon decompression.

It is an object of the invention to provide a method and system of decreasing transthoracic impedance for cardioversion and defibrillation, wherein the diameter of the patient body interface is optimized to provide even pressure over common defibrillator patches that have an average size of between 10 and 14 centimeters in diameter.

It is an object of the invention to provide a method and system of decreasing transthoracic impedance for cardioversion and defibrillation, wherein the rigid lower plate defines a plane orthogonal to the direction vector of compression application of said device and includes implements which secure a contiguous junction to a patient body interface on its lower side and a component encasing or compression zone on its upper side.

It is an object of the invention to provide a method and system of decreasing transthoracic impedance as in claim 1, wherein the compression zone has a circular periphery and wherein are enclosed semi-elastic mechanisms such as a plurality of tuned spring or damping mechanisms comprised of pneumatic and or hydraulic systems so as to allow a customizable rigidity to be achieved.

It is an object of the invention to provide a method and system of decreasing transthoracic impedance, wherein a force feedback system comprises of a mechanical and or electrical system to gauge the pressure being exerted by the device on the patient body.

These and other objects of the invention will become more apparent in the description below.

SUMMARY OF THE INVENTION

The present invention provides a novel method and system to reduce transthoracic impedance through the application of standardized pressure over desired electrode patches before delivering a defibrillator shock when performing cardioversions and defibrillations.

The system, which provides a way for users to manually apply standardized pressure over electrode patches before shock delivery, comprises of a circular depressor device with handle, akin to former models of manual defibrillator paddles, the predecessor of the current adhesive electrode patches. The bottom of said device consists of a deformable material herein defined as the device's "patient body interface." This feature provides a means for soft-tissue compliance in providing an even distribution of pressure when using said device, resulting in the uniform application of pressure over desired electrode patches. The patient body interface of the device is integrated with the body or main component encasing of the device, herein defined as a "compression zone" in which a plurality of tuned spring or spring like mechanisms, notwithstanding the possibility of pneumatic and or hydraulic suspension systems, are enclosed.

Incorporated into the compression zone of the device are a mechanical force gauge system and or electrical microcontroller system with power source and accompanying implements such as a piezoresistive sensor which senses the force of compression while the device is in contact with the patient and applying pressure. The system is calibrated to return visual and or audio feedback to the user, and gives indication of pressure in a qualitative and or quantitative manner through a user interface on the top plate—herein defined as the face of the device proximal to the handle of the device—upon sufficiently applied pressure to the patient body. Once sufficient pressure is achieved, the user can move to a subsequent desired electrode patch and use the device with the same process to further decrease the effective transthoracic impedance of the patient before shock delivery. All external components of the device are constructed of plastics and other electrically insulated materials to provide an additional safety margin for users interacting with patients who are electrically in circuit with operating defibrillators.

BRIEF DESCRIPTION OF THE DRAWINGS

The embodiment of the invention will be better understood by the following referenced figures in which.

DETAILED DESCRIPTION OF THE INVENTION

The operation of the preferred embodiment of the device is as follows: the user turns on the device using the power switch in the user interface and chooses the two desired external adhesive electrode patches on the patient between which a defibrillator shock will be delivered. The center of the device will be aligned over the center of the first patch so as to provide the most even pressure distribution, and the user will proceed to depress the patient body interface of the device against the patch. The device will be compressed by the user against the first patch until the full lighting of an LED array accompanied by an audio cue from the user interface of the device signifies that the threshold pressure that optimizes the electrode patch to skin contact has been achieved. Upon this signal, the user would immediately release pressure over the first patch, align the center of the device over the center of the second desired patch, and repeat the depression process for the second patch. Upon the successful application of standardized pressure over both patches, the user can step away from the patient and follow standard protocols in delivering a defibrillator shock.

If subsequent shocks are needed, the user can repeat the pressure application process over the desired electrode patches as desired in between shock deliveries.

Figure 1:
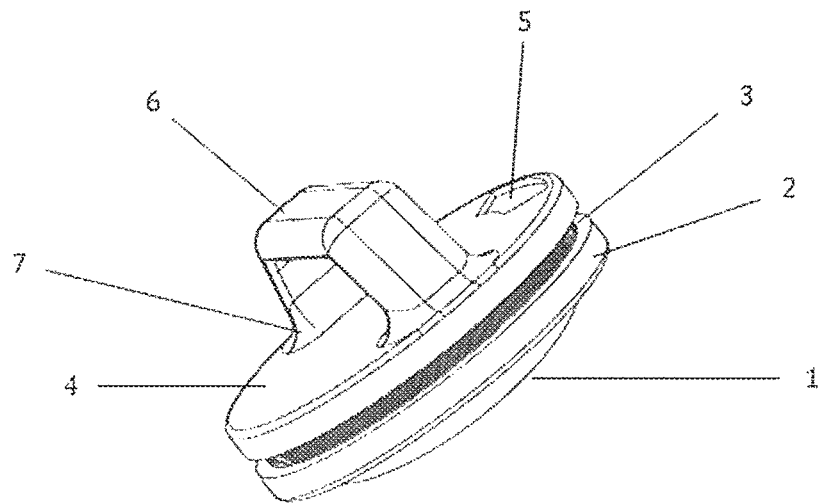
FIG. 1 is an overview of the device.

Referring now to FIG. 1, there is displayed an overview of the device. The bottom of the device (1) consists of the interface to the patient body that is composed of a deformable material to provide soft-tissue compliance and even pressure distribution. This interface is contiguous with the bottom plate (2) of the device, which provides a rigid interface between the deformable material and the body of the device. This rigid plate forms the bottom of the compression zone (3) which encloses the mechanical or electrical sensing components and power source of the pressure sensing system and is constructed in a way as to allow tuned compression between the top plate (4) and the bottom plate (2). The characteristics of the compression achievable in the compression zone are determined in part by the tuning of the spring-like materials and mechanisms enclosed inside the collapsible casing of the compression zone. A user interface (5) is embedded in the top plate (4) and provides qualitative and or quantitative feedback in the form of visual and or audio cues to notify the user when sufficient force has been applied to patches, in addition to a power switch in the electronic embodiment of the device. A handle (6) is incorporated with the top plate through a reinforced base component (7) to ensure durability of the interface between the handle and the body of the device.

Figure 2:
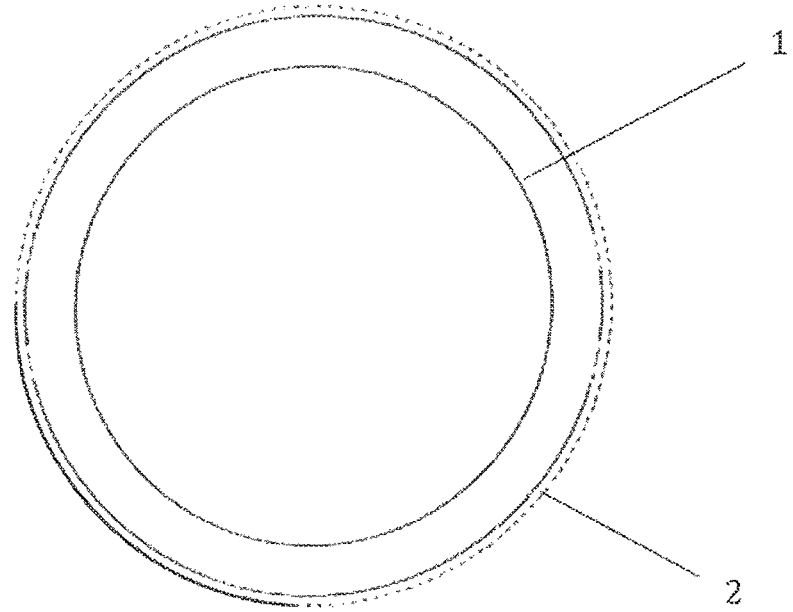
FIG. 2 is a bottom view of the device.

Referring now to FIG. 2, there is displayed the relation in size of the patient body interface (1) and the bottom plate (2). It is shown that the deformable material which constitutes the patient body interface composes a smaller surface area than the bottom plate so as to ensure that the junction between the interface and the bottom plate is removed from the external edge of the device (2). This feature is incorporated to reduce wear on the interface to bottom edge junction. The surface area of the patient body interface is designed to cover the optimal electrode patch sizes of 10 to 14 cm in diameter.

Figure 3:
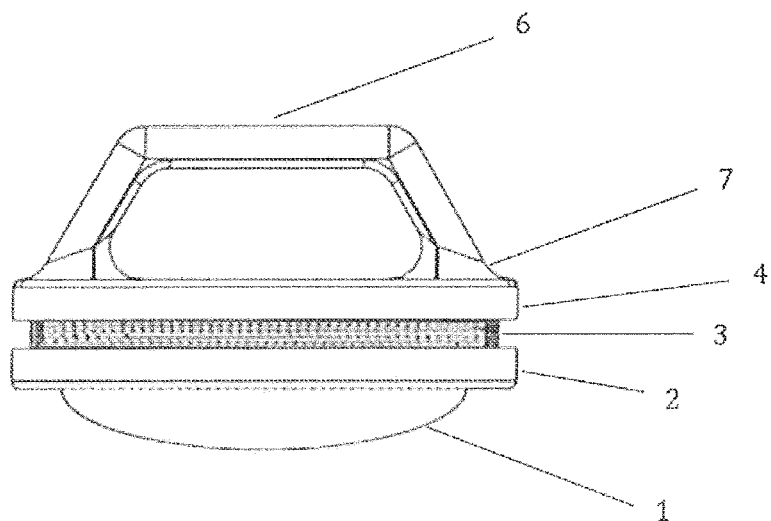
FIG. 3 is a front view of the device.

Referring now to FIG. 3, there is displayed the relation between the different components of the device in its uncompressed state. It is shown that the patient body interface material is uncompressed (1) and that the compression zone is uncompressed (3) to achieve a resting distance between the top and bottom plates (2, 4).

Figure 4:
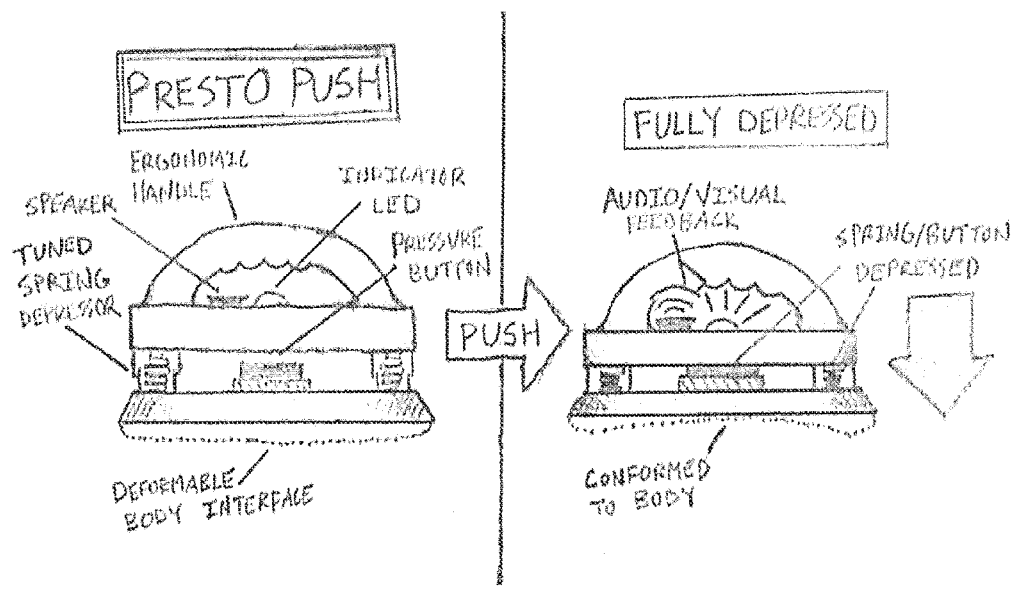
FIG. 4 is a characterization of a preferred embodiment of the device in operation.

Referring now to FIG. 4, a preferred functional embodiment of the device is displayed. The left half of the figure shows the internal components of the compression zone with a set of tuned springs and a piezoresistive sensor, referred to as a "pressure button." A particular electronic embodiment of the user interface is shown, with an indicator LED and incorporated speaker. Ergonomic handle can be seen, as well as the undeformed patient body interface. Upon full depression of the device by the user, the patient body interface deforms to the patient and the top plate comes into contact with the pressure button. Visual and auditory feedback to the user is provided upon the pressure button and accompanying microcontroller system sensing the crossing of a threshold voltage value due to applied force.

What is claimed is:

1. A system for decreasing transthoracic impedance for cardioversion and defibrillation comprising:
   a compression zone having a top surface and a bottom surface;
   a rigid bottom plate having an upper surface attached to the bottom surface of the compression zone and a lower surface;
   a top plate attached to the top surface of the compression zone, wherein the top plate has a handle and an embedded user interface that provides feedback to a user;
   semi-elastic mechanisms or materials and a force feedback system enclosed in the compression zone; and
   a deformable patient body interface attached to the lower surface of the rigid bottom plate,
   wherein, when the deformable patient body interface is compressed against a patient's body with a standardized calibrated threshold force, an indicator cue will notify the user.

2. The system of claim 1, wherein the deformable patient body interface comprises an elastic, moldable, or elastic and moldable material which comforms to non-uniform surfaces upon compression and can return to its original shape upon decompression.

3. The system of claim 2, wherein the diameter of the patient body interface is optimized to provide even pressure over common defibrillator patches that have an average size of between 10 and 14 centimeters in diameter.

4. The system of claim 1, wherein the rigid lower plate defines a plane orthogonal to the direction vector of compression application of said device and includes implements which secure a contiguous junction to a patient body interface on its lower side and a component encasing or compression zone on its upper side.

5. The system of claim 1, wherein the compression zone has a circular periphery and wherein are enclosed semi-elastic mechanisms comprised of pneumatic, hydraulic, or pneumatic and hydraulic systems to allow a customizable rigidity to be achieved.

6. The system of claim 1, wherein a force feedback system comprises a mechanical, electrical, or mechanical and electrical system to gauge the pressure being exerted by the device on the patient body.

7. The system of claim 6, wherein a top plate incorporates a user interface that provides quantitative, qualitative, or quantitative and qualitative indication of the force being exerted on the patient's body.

8. The system of claim 7, wherein an array of Light Emitting Diodes are operated by a microcontroller system that is receiving the voltage or current signal to detect the force sensed from a piezoresistive sensor.

9. The system of claim 8, wherein an audio cue is also played upon the reaching of a threshold force reading.

10. A method of decreasing transthoracic impedance for cardioversion and defibrillation comprising:
    positioning a system of claim 1 on a patient's chest and applying sufficient pressure to the handle to cause cardioversion or defibrillation.

11. The method of claim 10, wherein the deformable patient body interface is comprised of an elastic and or moldable material which comforms to non-uniform surfaces upon compression and can return to its original shape upon decompression.

12. The method of claim 10, wherein the rigid lower plate defines a plane orthogonal to the direction vector of compression application of said device and includes implements which secure a contiguous junction to a patient body interface on its lower side and a component encasing or compression zone on its upper side.

13. The method of claim 10, wherein the compression zone has a circular periphery and wherein are enclosed semi-elastic mechanisms comprise pneumatic, hydraulic, or pneumatic and hydraulic systems to allow a customizable rigidity to be achieved.

14. The method of 10, wherein a force feedback system comprises of mechanical, electrical, or mechanical and electrical system to gauge the pressure being exerted by the device on the patient body.

15. The method of claim 10, wherein an array of Light Emitting Diodes is operated by a microcontroller system that is receiving the voltage or current signal to detect the force sensed from a piezoresistive sensor.

16. The method of claim 15, wherein an audio cue is played when a threshold force reading is reached.

* * * * *